(12) United States Patent
Vaidya et al.

(10) Patent No.: US 11,610,304 B2
(45) Date of Patent: Mar. 21, 2023

(54) PREDICTING TUMOR PROGNOSES BASED ON A COMBINATION OF RADIOMIC AND CLINICO-PATHOLOGICAL FEATURES

(71) Applicant: Case Western Reserve University, Cleveland, OH (US)

(72) Inventors: Pranjal Vaidya, Cleveland, OH (US); Anant Madabhushi, Shaker Heights, OH (US); Kaustav Bera, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 163 days.

(21) Appl. No.: 17/068,089

(22) Filed: Oct. 12, 2020

(65) Prior Publication Data

US 2021/0110540 A1   Apr. 15, 2021

Related U.S. Application Data

(60) Provisional application No. 62/913,879, filed on Oct. 11, 2019.

(51) Int. Cl.
*G06T 7/00* (2017.01)
*G06T 7/11* (2017.01)
(Continued)

(52) U.S. Cl.
CPC .......... *G06T 7/0012* (2013.01); *A61B 5/7267* (2013.01); *A61B 5/7275* (2013.01);
(Continued)

(58) Field of Classification Search
CPC ............... G06T 7/0012; G06T 7/11; G06T 2207/20081; G06T 2207/20084;
(Continued)

(56) References Cited

U.S. PATENT DOCUMENTS

2009/0280479 A1* 11/2009 Hoon .................. C12Q 1/6806
435/6.12
2017/0351939 A1* 12/2017 Madabhushi ......... G06T 7/0012
(Continued)

FOREIGN PATENT DOCUMENTS

WO    WO-2021030784 A1 *  2/2021

*Primary Examiner* — Jon Chang
(74) *Attorney, Agent, or Firm* — Eschweiler & Potashnik, LLC (57) ABSTRACT

Embodiments discussed herein facilitate building and/or employing a clinical-radiomics score for determining tumor prognoses based on a combination of a radiomics risk score generated by a machine learning model and clinico-pathological factors. One example embodiment can perform actions comprising: accessing a medical imaging scan of a tumor; segmenting a peri-tumoral region around the tumor; extracting one or more intra-tumoral radiomic features from the tumor and one or more peri-tumoral radiomic features from the peri-tumoral region; providing the one or more intra-tumoral radiomic features and the one or more peri-tumoral radiomic features to a trained machine learning model; receiving a radiomic risk score (RRS) associated with the tumor from the machine learning model; determining a clinical-radiomics score based on the RRS and one or more clinico-pathological factors; and generating a prognosis for the tumor based on the clinical-radiomics score.

20 Claims, 3 Drawing Sheets

(51) Int. Cl.
 *A61B 5/00* (2006.01)
 *G06N 3/04* (2023.01)
(52) U.S. Cl.
 CPC ............... *G06N 3/04* (2013.01); *G06T 7/11* (2017.01); *A61B 2576/00* (2013.01); *G06T 2207/20081* (2013.01); *G06T 2207/20084* (2013.01); *G06T 2207/30061* (2013.01); *G06T 2207/30096* (2013.01)
(58) Field of Classification Search
 CPC . G06T 2207/30061; G06T 2207/30096; A61B 5/7267; A61B 5/7275; A61B 2576/00; G06N 3/04
 See application file for complete search history.

(56) References Cited

U.S. PATENT DOCUMENTS

2019/0254611 A1* 8/2019 Madabhushi .......... G06K 9/627
2021/0035296 A1* 2/2021 Mahrooghy ......... A61B 8/4281

* cited by examiner

PREDICTING TUMOR PROGNOSES BASED ON A COMBINATION OF RADIOMIC AND CLINICO-PATHOLOGICAL FEATURES

CROSS REFERENCE TO RELATED APPLICATIONS

This application claims the benefit of U.S. Provisional Patent Application No. 62/913,879 filed Oct. 11, 2019, entitled "INTEGRATED CLINICO-RADIOMIC NOMOGRAM FOR PREDICTING DISEASE FREE SURVIVAL (DFS) IN STAGE I AND II EARLY STAGE NON-SMALL CELL LUNG CANCER (NSCLC)", the contents of which are herein incorporated by reference in their entirety.

BACKGROUND

Lung cancer is one of the most significant cause of cancer related deaths in both men as well as women. Annually, there are approximately 228,820 new lung cancer cases and 135,720 estimated deaths in the United States alone. Broadly lung cancer can be divided into small cell and non-small cell lung cancer (NSCLC) where NSCLC accounts for almost 85% of total cases. Early stage accounts for stage IA to IIB diseases and significant proportion of these patients have recurrent disease even after curative resection.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Various embodiments discussed herein can build and/or employ a clinical-radiomics score for determining tumor prognoses based on a combination of a radiomics risk score generated by a machine learning model and clinico-pathological factors.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
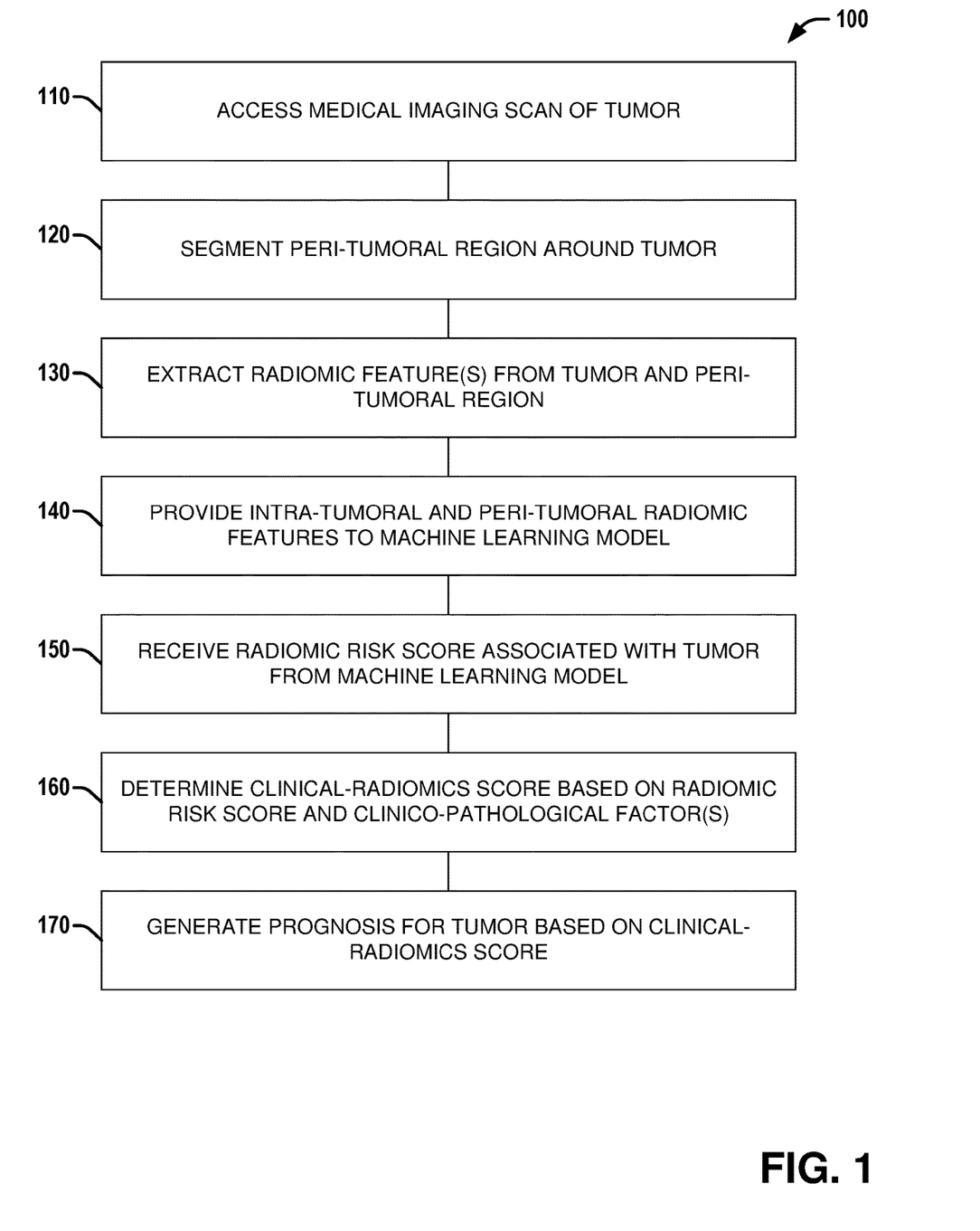
FIG. 1 illustrates a flow diagram of an example method/set of operations that can be performed by one or more processors to predict a prognosis for a tumor based on a clinical-radiomics score constructed from a combination of a radiomics risk score generated by a machine learning model and clinico-pathological factors, according to various embodiments discussed herein.

Referring to FIG. 1, illustrated is a flow diagram of an example method/set of operations 100 that can be performed by one or more processors to predict a prognosis for a tumor based on a clinical-radiomics score constructed from a combination of a radiomics risk score generated by a machine learning model and clinico-pathological factors, according to various embodiments discussed herein. Processor(s) can include any combination of general-purpose processors and dedicated processors (e.g., graphics processors, application processors, etc.). The one or more processors can be coupled with and/or can include memory or storage and can be configured to execute instructions stored in the memory or storage to enable various apparatus, applications, or operating systems to perform the operations. The memory or storage devices may include main memory, disk storage, or any suitable combination thereof. The memory or storage devices can comprise—but is not limited to—any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 can comprise, at 110, accessing a medical imaging scan (e.g., MRI (contrast MRI, etc.), CT, etc.) of a tumor (e.g., segmented via expert annotation, computer segmentation (e.g., via deep learning, etc.), etc.). In various embodiments and in the example use case discussed below, the medical imaging scan can be obtained via a system and/or apparatus implementing the set of operations 100, or can be obtained from a separate medical imaging system (e.g., a MRI system/apparatus, a CT system/apparatus, etc.). Additionally, the medical imaging scan can be accessed contemporaneously with or at any point prior to performing the set of operations 100.

The set of operations 100 can further comprise, at 120, segmenting a peri-tumoral region around the tumor.

The set of operations 100 can further comprise, at 130, extracting one or more intra-tumoral radiomic features from the tumor and one or more peri-tumoral radiomic features from the peri-tumoral region.

The set of operations 100 can further comprise, at 140, providing the one or more intra-tumoral radiomic features and the one or more peri-tumoral radiomic features to a trained machine learning model.

The set of operations 100 can further comprise, at 150, receiving a radiomic risk score (RRS) associated with the tumor from the machine learning model.

The set of operations 100 can further comprise, at 160, determining a clinical-radiomics score based on the RRS and one or more clinico-pathological factors.

The set of operations 100 can further comprise, at 170, generating a prognosis for the tumor based on the clinical-radiomics score (e.g., via a nomogram, etc.).

Figure 2:
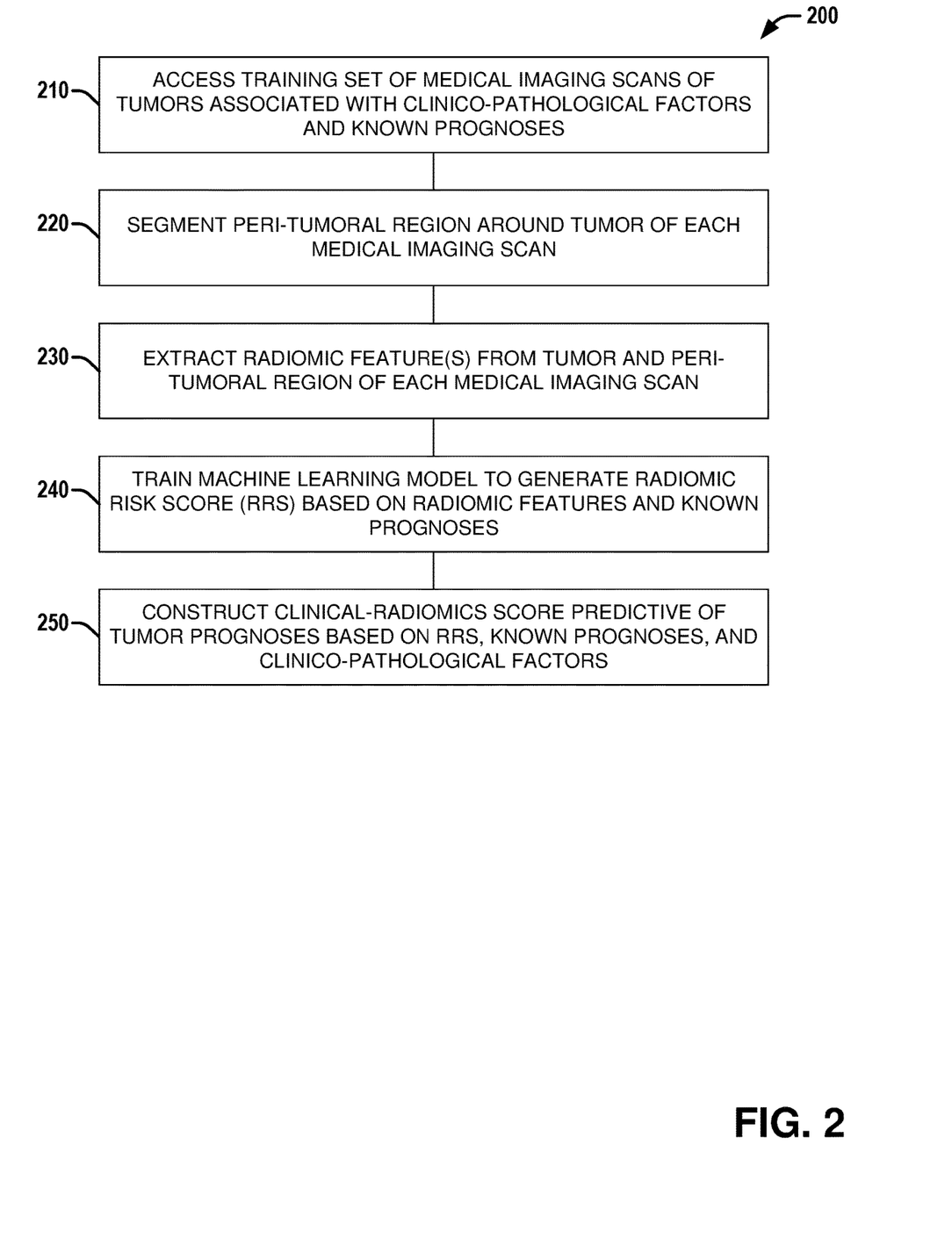
FIG. 2 illustrates a flow diagram of an example method/set of operations that can be performed by one or more processors to build a clinical-radiomics score based on a combination of a radiomics risk score generated by a machine learning model and clinico-pathological factors, according to various embodiments discussed herein.

Referring to FIG. 2, illustrated is a flow diagram of an example method/set of operations 200 that can be performed by one or more processors to build a clinical-radiomics score based on a combination of a radiomics risk score generated by a machine learning model and clinico-pathological factors, according to various embodiments discussed herein.

The set of operations 200 can comprise, at 210, accessing a training set of medical imaging scans of tumors, wherein each medical imaging scan is associated with a known prognosis for that tumor and an associated set of clinico-pathological factors. In various embodiments and in the example use case discussed below, the training set of medical imaging scans can be obtained via a system and/or apparatus implementing the set of operations 200, or can be obtained from a separate medical imaging system. Additionally, the training set can be accessed contemporaneously with or at any point prior to performing the set of operations 200.

The set of operations 200 can further comprise, at 220, for each medical imaging scan of the training set, segmenting a peri-tumoral region around the tumor of that medical imaging scan.

The set of operations 200 can further comprise, at 230, for each medical imaging scan of the training set, extracting one or more intra-tumoral radiomic features from the tumor of that medical imaging scan and one or more peri-tumoral radiomic features from the peri-tumoral region of that medical imaging scan.

The set of operations 200 can further comprise, at 240, for each medical imaging scan of the training set, training a machine learning model to generate a radiomic risk score (RRS) based on the known prognosis associated with the tumor of that medical imaging scan, the one or more intra-tumoral radiomic features from the tumor of that medical imaging scan, and the one or more peri-tumoral radiomic features from the peri-tumoral region of that medical imaging scan.

The set of operations 200 can further comprise, at 250, for each medical imaging scan of the training set, construct a clinical-radiomics score predictive of tumor prognoses based on the RRS, the one or more clinico-pathological factors for the tumor of that medical imaging scan, and the known prognosis for the tumor of that medical imaging scan. Additionally, in some embodiments, a nomogram can be constructed to visually represent the connection between RRS, clinical-radiomics score, and tumor prognosis (e.g., likelihood or not of DFS post-treatment (e.g., surgery, etc.)).

Additional aspects and embodiments are discussed below in connection with the following example use case.

Example Use Case: Integrated Clinico-Radiomic Nomogram for Predicting Disease-Free Survival (DFS) in Stage I and II Early Stage Non-Small Cell Lung Cancer (ES-NSCLC)

The following discussion provides example embodiments in connection with an example use case involving building and/or employing a clinical-radiomics score for early stage non-small cell lung cancer (ES-NSCLC) based on a combination of a radiomics risk score generated by a machine learning model and clinico-pathological factors.

Background: ES-NSCLC comprises about 45% of all NSCLC patients, with 5-year survival ranging between 30-49%. Surgical resection is the standard of care curative modality in these patients but about 30-55% of patients often recur following surgery within the first 3 years. There is currently no validated method to stratify patients based on their risk of recurrence following surgery in these patients. The example use case developed and validated a nomogram using a combination of CT-derived radiomic textural features and clinico-pathologic factors, in order to predict Disease-Free Survival (DFS) in ES-NSCLC.

Methods: This study comprised 350 ES-NSCLC patients from two different institutions who underwent surgery (75 patients relapsed). Radiomic textural features were extracted from tumor region (Intratumoral—IT) as well as from the annular ring shaped peritumoral region (PT) with 3 mm as a ring thickness and extending 9 mm outside the nodule. A total of 124 features from Gabor, Laws, Laplace, Haralick and Collage feature families were extracted from IT and each PT ring (e.g., 0-3 mm, 3-6 mm, 6-9 mm) for all patients. The most stable, significant and uncorrelated features were selected from $D_1$ (N=221) and used to build a Lasso (least absolute shrinkage and selection operator)-regularized multivariate Cox-regression model to generate a Radiomic Risk Score (RRS) derived from weighted Lasso coefficients. Further, the RRS was integrated with clinico-pathologic variables (Lympho-vascular invasion (LVI) and American Joint Committee on Cancer (AJCC) stage) which were independently predictive on DFS in multivariate analysis to build a clinical-radiomics score (CRS). A nomogram was constructed to visually assess the CRS and RRS on DFS. Performances were evaluated using hazard ratios (HR), concordance index (CI) along with decision and calibration curves to show the differences between the individual and integrated risk scores.

Results: The top 14 radiomic features included 6 from IT and 8 from 0-9 mm PT distance. The constructed RRS could predict DFS (n=221, C-index=0.69, HR=3.8, $p<0.05$) on training (D1) and (n=129, C-index=0.69, HR—2.5) on a blinded validation cohort ($D_2$). The addition of LVI and pN to build the CRS increased the C-index=0.74, $p<0.05$. Decision and calibration curve analysis shows improved performance of CRS over RRS or clinico-pathologic factors alone.

Conclusion: Addition of prognostic clinical factors (LVI, AJCC stage) improved the performance of the Radiomic Risk Score model in order to accurately predict DFS in ES-NSCLC patients undergoing surgery.

Additional Embodiments

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein relate to training and/or employing machine learning models (e.g., unsupervised (e.g., clustering) or supervised (e.g., classifiers, etc.) models) to determine a prognosis (e.g., likelihood of disease-free survival) for a tumor based at least in part on features of medical imaging scans (e.g., MRI, CT, etc.) that are not perceivable by the human eye, and involve computation that cannot be practically performed in the human mind. As one example, machine learning classifiers and/or deep learning models as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance of the machine, computer, or system with which embodiments are implemented.

Figure 3:
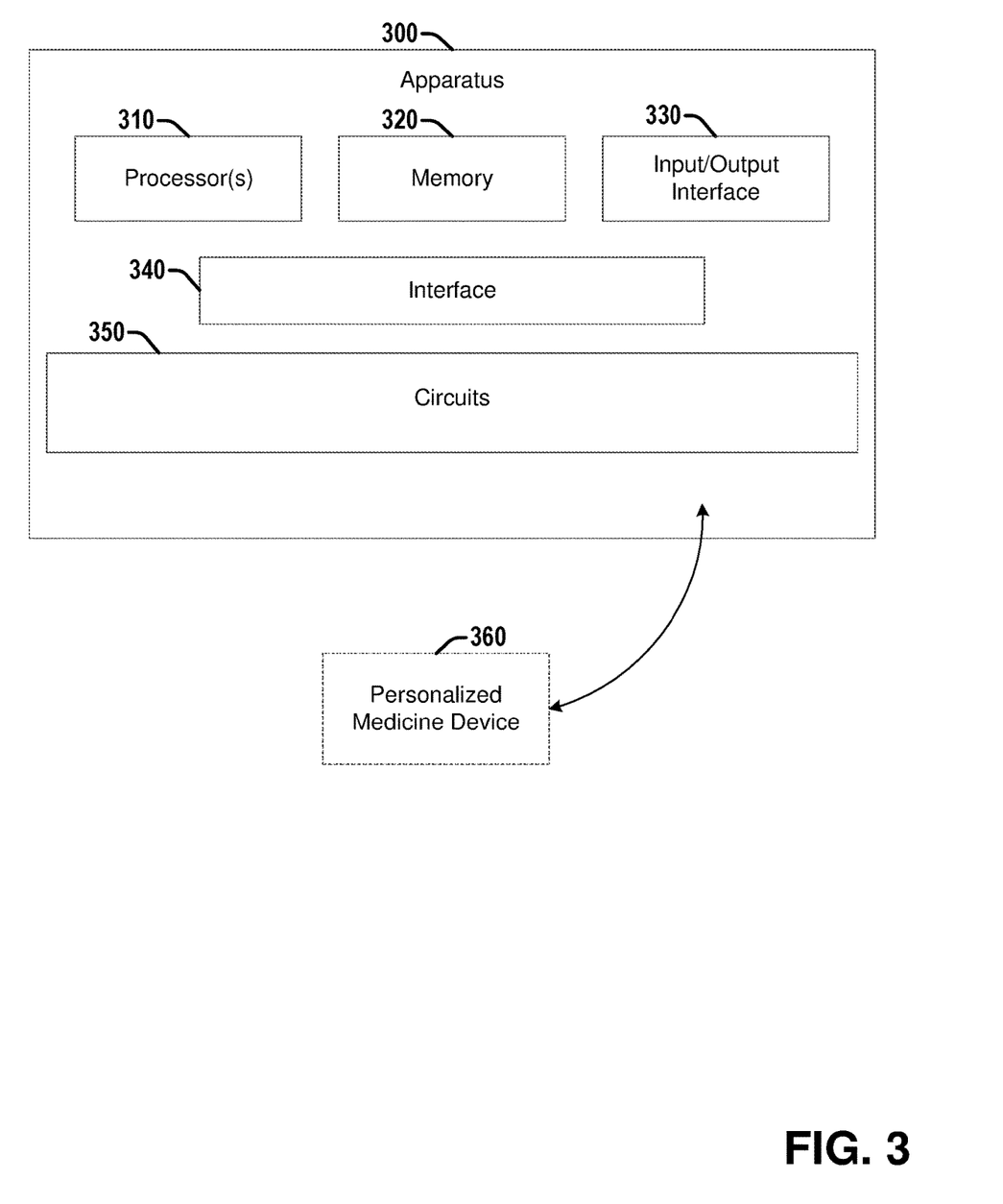
FIG. 3 illustrates a diagram of an example apparatus that can facilitate building and/or employing a clinical-radiomics score based on a combination of a radiomics risk score generated by a machine learning model and clinico-pathological factors, according to various embodiments discussed herein.

Referring to FIG. 3, illustrated is a diagram of an example apparatus 300 that can facilitate building and/or employing a clinical-radiomics score based on a combination of a radiomics risk score generated by a machine learning model and clinico-pathological factors, according to various embodiments discussed herein. Apparatus 300 can be configured to perform various techniques discussed herein, for example, various operations discussed in connection with sets of operations 100 and/or 200. Apparatus 300 can comprise one or more processors 310 and memory 320. Processor(s) 310 can, in various embodiments, comprise circuitry such as, but not limited to, one or more single-core or multi-core processors. Processor(s) 310 can include any combination of general-purpose processors and dedicated processors (e.g., graphics processors, application processors, etc.). The processor(s) can be coupled with and/or can comprise memory (e.g., of memory 320) or storage and can be configured to execute instructions stored in the memory 320 or storage to enable various apparatus, applications, or operating systems to perform operations and/or methods discussed herein. Memory 320 can be configured to store medical imaging scan(s) (e.g., CT, MRI, etc.) Each of the medical imaging scan(s) can comprise a plurality of pixels or voxels, each pixel or voxel having an associated intensity. Memory 320 can be further configured to store additional data involved in performing operations discussed herein, such as radiomic and/or clinical features, or other information employed in various methods (e.g., 100, 200, etc.) discussed in greater detail herein.

Apparatus 300 can also comprise an input/output (I/O) interface 330 (e.g., associated with one or more I/O devices), a set of circuits 350, and an interface 340 that connects the processor(s) 310, the memory 320, the I/O interface 330, and the set of circuits 350. I/O interface 330 can be configured to transfer data between memory 320, processor 310, circuits 350, and external devices, for example, a medical imaging device (e.g., CT system, MRI system, etc.), and/or one or more remote devices for receiving inputs and/or providing outputs to a clinician, patient, etc., such as optional personalized medicine device 360.

The processor(s) 310 and/or one or more circuits of the set of circuits 350 can perform one or more acts associated with a method or set of operations discussed herein, such as set of operations 100 and/or 200. In various embodiments, different acts (e.g., different operations of a set of operations) can be performed by the same or different processor(s) 310 and/or one or more circuits of the set of circuits 350.

Apparatus 300 can optionally further comprise personalized medicine device 360. Apparatus 300 can be configured to provide a prognosis (e.g., prediction related to disease-free survival, etc.) for a patient determined based at least in part on a combination of intra-tumoral radiomic features, peri-tumoral radiomic features, and/or clinical features as discussed herein, and/or other data to personalized medicine device 360. Personalized medicine device 360 may be, for example, a computer assisted diagnosis (CADx) system or other type of personalized medicine device that can be used to facilitate monitoring and/or treatment of an associated medical condition. In some embodiments, processor(s) 310 and/or one or more circuits of the set of circuits 350 can be further configured to control personalized medicine device 360 to display the prognosis for a clinician or the patient or other data on a computer monitor, a smartphone display, a tablet display, or other displays.

Examples herein can include subject matter such as an apparatus, a medical image system/apparatus, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for generating system-independent quantitative perfusion measurements, according to embodiments and examples described.

Example 1 is a non-transitory computer-readable medium storing computer-executable instructions that, when executed, cause a processor to perform operations, comprising: accessing a medical imaging scan of a tumor; segmenting a peri-tumoral region around the tumor; extracting one or more intra-tumoral radiomic features from the tumor and one or more peri-tumoral radiomic features from the peri-tumoral region; providing the one or more intra-tumoral radiomic features and the one or more peri-tumoral radiomic features to a trained machine learning model; receiving a radiomic risk score (RRS) associated with the tumor from the machine learning model; determining a clinical-radiomics score based on the RRS and one or more clinico-pathological factors; and generating a prognosis for the tumor based on the clinical-radiomics score.

Example 2 comprises the subject matter of any variation of any of example(s) 1, wherein the prognosis is one of disease-free survival (DFS), non-DFS, or a likelihood of DFS.

Example 3 comprises the subject matter of any variation of any of example(s) 1-2, wherein at least one of the one or more intra-tumoral radiomic features or the peri-tumoral radiomic features comprise a first-order statistic of one or more of the following, extracted from the one of the medical imaging scan or the medical imaging scan after transformation with one of a filter or a wavelet decomposition: at least one Laws energy measure, at least one Gabor feature, at least one Haralick feature, at least one Laplace feature, at least one Co-occurrence of Local Anisotropic Gradient Orientations (CoLIAGe) feature, at least one Gray Level Size Zone Matrix, at least one Gray Level Run Length Matrix, at least one Neighboring Gray Tone Difference Matrix, at least one raw intensity value, at least one quantitative pharmacokinetic parameter, at least one semi-quantitative pharmacokinetic parameter, at least one Gray Level Dependence Matrix, at least one shape feature, or at least one feature from at least one pre-trained Convolutional Neural Network (CNN).

Example 4 comprises the subject matter of any variation of any of example(s) 3, wherein the first-order statistic is one of a mean, a median, a standard deviation, a skewness, a kurtosis, a range, a minimum, a maximum, a percentile, or histogram frequencies.

Example 5 comprises the subject matter of any variation of any of example(s) 1-4, wherein the peri-tumoral region comprises a plurality of concentric peri-tumoral rings around the tumor, wherein the one or more peri-tumoral radiomic features comprise at least one peri-tumoral radiomic feature extracted from each peri-tumoral ring of the plurality of concentric peri-tumoral rings.

Example 6 comprises the subject matter of any variation of any of example(s) 5, wherein each peri-tumoral ring of the plurality of concentric peri-tumoral rings has a width between 2 mm and 4 mm.

Example 7 comprises the subject matter of any variation of any of example(s) 1-6, wherein the tumor is an early-stage non-small cell lung cancer (ES-NSCLC) tumor.

Example 8 comprises the subject matter of any variation of any of example(s) 1-7, wherein the machine learning model is one of, or an ensemble of two or more of: a least absolute shrinkage and selection operator (Lasso)-regularized multivariate Cox-regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, a LASSO model, an elastic net, a Gaussian process classification, or a nearest neighbors classification.

Example 9 comprises the subject matter of any variation of any of example(s) 1-8, wherein the one or more clinico-pathological factors comprise at least one of a lymphovascular invasion (LVI) or an American Joint Committee on Cancer (AJCC) stage.

Example 10 is an apparatus, comprising: a memory configured to store a medical imaging scan of a tumor; and one or more processors configured to: segment a peri-tumoral region around the tumor; extract one or more intra-tumoral radiomic features from the tumor and one or more peri-tumoral radiomic features from the peri-tumoral region; provide the one or more intra-tumoral radiomic features and the one or more peri-tumoral radiomic features to a trained machine learning model; receive a radiomic risk score (RRS) associated with the tumor from the machine learning model; determine a clinical-radiomics score based on the RRS and one or more clinico-pathological factors; and generate a prognosis for the tumor based on the clinical-radiomics score.

Example 11 comprises the subject matter of any variation of any of example(s) 10, wherein the prognosis is one of disease-free survival (DFS), non-DFS, or a likelihood of DFS.

Example 12 comprises the subject matter of any variation of any of example(s) 10-11, wherein at least one of the one or more intra-tumoral radiomic features or the peri-tumoral radiomic features comprise a first-order statistic of one or more of the following, extracted from the one of the medical imaging scan or the medical imaging scan after transformation with one of a filter or a wavelet decomposition: at least one Laws energy measure, at least one Gabor feature, at least one Haralick feature, at least one Laplace feature, at least one Co-occurrence of Local Anisotropic Gradient Orientations (CoLIAGe) feature, at least one Gray Level Size Zone Matrix, at least one Gray Level Run Length Matrix, at least one Neighboring Gray Tone Difference Matrix, at least one raw intensity value, at least one quantitative pharmacokinetic parameter, at least one semi-quantitative pharmacokinetic parameter, at least one Gray Level Dependence Matrix, at least one shape feature, or at least one feature from at least one pre-trained Convolutional Neural Network (CNN).

Example 13 comprises the subject matter of any variation of any of example(s) 12, wherein the first-order statistic is one of a mean, a median, a standard deviation, a skewness, a kurtosis, a range, a minimum, a maximum, a percentile, or histogram frequencies.

Example 14 comprises the subject matter of any variation of any of example(s) 10-13, wherein the peri-tumoral region comprises a plurality of concentric peri-tumoral rings around the tumor, wherein the one or more peri-tumoral radiomic features comprise at least one peri-tumoral radiomic feature extracted from each peri-tumoral ring of the plurality of concentric peri-tumoral rings.

Example 15 comprises the subject matter of any variation of any of example(s) 14, wherein each peri-tumoral ring of the plurality of concentric peri-tumoral rings has a width between 2 mm and 4 mm.

Example 16 comprises the subject matter of any variation of any of example(s) 10-15, wherein the tumor is an early-stage non-small cell lung cancer (ES-NSCLC) tumor.

Example 17 comprises the subject matter of any variation of any of example(s) 10-16, wherein the machine learning model is one of, or an ensemble of two or more of: a least absolute shrinkage and selection operator (Lasso)-regularized multivariate Cox-regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, a LASSO model, an elastic net, a Gaussian process classification, or a nearest neighbors classification.

Example 18 is a non-transitory computer-readable medium storing computer-executable instructions that, when executed, cause a processor to perform operations, comprising: accessing a training set comprising a plurality of medical imaging scans, wherein each medical imaging scan comprises an associated tumor of that medical imaging scan, and wherein, for each medical imaging scan, the associated tumor is associated with a known prognosis and one or more known clinico-pathological factors; for each medical imaging scan of the training set: segmenting a peri-tumoral region around the tumor of that medical imaging scan; extracting one or more intra-tumoral radiomic features from the tumor of that medical imaging scan and one or more peri-tumoral radiomic features from the peri-tumoral region of that medical imaging scan; training a machine learning model to generate a radiomic risk score (RRS) based on the known prognosis associated with the tumor of that medical imaging scan, the one or more intra-tumoral radiomic features from the tumor of that medical imaging scan, and the one or more peri-tumoral radiomic features from the peri-tumoral region of that medical imaging scan; and construct a clinical-radiomics score predictive of tumor prognoses based on the RRS, the one or more clinico-pathological factors for the tumor of that medical imaging scan, and the known prognosis for the tumor of that medical imaging scan.

Example 19 comprises the subject matter of any variation of any of example(s) 18, wherein the prognosis is one of disease-free survival (DFS), non-DFS, or a likelihood of DFS, and wherein, for each medical imaging scan of the training set, the associated tumor is an early-stage non-small cell lung cancer (ES-NSCLC) tumor.

Example 20 comprises the subject matter of any variation of any of example(s) 18-19, wherein at least one of the one or more intra-tumoral radiomic features or the peri-tumoral radiomic features comprise a first-order statistic of one or more of the following, extracted from one of that medical imaging scan or that medical imaging scan after transformation with one of a filter or a wavelet decomposition: at least one Laws energy measure, at least one Gabor feature, at least one Haralick feature, at least one Laplace feature, at least one Co-occurrence of Local Anisotropic Gradient Orientations (CoLIAGe) feature, at least one Gray Level Size Zone Matrix, at least one Gray Level Run Length Matrix, at least one Neighboring Gray Tone Difference Matrix, at least one raw intensity value, at least one quantitative pharmacokinetic parameter, at least one semi-quantitative pharmacokinetic parameter, at least one Gray Level Dependence Matrix, at least one shape feature, or at least one feature from at least one pre-trained Convolutional Neural Network (CNN).

Example 21 comprises an apparatus comprising means for executing any of the described operations of examples 1-20.

Example 22 comprises a machine readable medium that stores instructions for execution by a processor to perform any of the described operations of examples 1-20.

Example 23 comprises an apparatus comprising: a memory; and one or more processors configured to: perform any of the described operations of examples 1-20.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:

accessing a medical imaging scan of a tumor;
segmenting a peri-tumoral region around the tumor;
extracting one or more intra-tumoral radiomic features from the tumor and one or more peri-tumoral radiomic features from the peri-tumoral region;
providing the one or more intra-tumoral radiomic features and the one or more peri-tumoral radiomic features to a trained machine learning model;
receiving a radiomic risk score (RRS) associated with the tumor from the trained machine learning model, wherein the trained machine learning model generates the RRS by applying a regression model to the one or more intra-tumoral radiomic features and the one or more peri-tumoral radiomic features; and
determining a clinical-radiomics score by integrating the RRS with one or more clinico-pathological factors.

2. The non-transitory computer-readable medium of claim 1, further comprising:
constructing a nomogram that visually represents a connection between the RRS and the clinical-radiomics score; and
predicting disease free survival for a patient having early stage non-small cell lung cancer (ES-NSCLC) based on the clinical-radiomics score and the RRS depicted in the nomogram.

3. The non-transitory computer-readable medium of claim 1, wherein at least one of the one or more intra-tumoral radiomic features or the peri-tumoral radiomic features comprise a first-order statistic of one or more of the following, extracted from the one of the medical imaging scan or the medical imaging scan after transformation with one of a filter or a wavelet decomposition: at least one Laws energy measure, at least one Gabor feature, at least one Haralick feature, at least one Laplace feature, at least one Co-occurrence of Local Anisotropic Gradient Orientations (CoLIAGe) feature, at least one Gray Level Size Zone Matrix, at least one Gray Level Run Length Matrix, at least one Neighboring Gray Tone Difference Matrix, at least one raw intensity value, at least one quantitative pharmacokinetic parameter, at least one semi-quantitative pharmacokinetic parameter, at least one Gray Level Dependence Matrix, at least one shape feature, or at least one feature from at least one pre-trained Convolutional Neural Network (CNN).

4. The non-transitory computer-readable medium of claim 1, further comprising:
extracting a first number of radiomic features from the tumor and the peri-tumoral regions; and
generating the RRS from a sub-set of the first number of radiomic features that is less than the first number of radiomic features, wherein the sub-set comprises the one or more intra-tumoral radiomic features and the one or more peri-tumoral radiomic features, the one or more peri-tumoral radiomic features being a larger number of features than the one or more intra-tumoral radiomic features.

5. The non-transitory computer-readable medium of claim 1, wherein the peri-tumoral region comprises a plurality of concentric peri-tumoral rings around the tumor, wherein the one or more peri-tumoral radiomic features comprise at least one peri-tumoral radiomic feature extracted from each peri-tumoral ring of the plurality of concentric peri-tumoral rings.

6. The non-transitory computer-readable medium of claim 5, wherein each peri-tumoral ring of the plurality of concentric peri-tumoral rings has a width between 2 mm and 4 mm.

7. The non-transitory computer-readable medium of claim 1, wherein the tumor is an early-stage non-small cell lung cancer (ES-NSCLC) tumor.

8. The non-transitory computer-readable medium of claim 1, wherein the trained machine learning model is one of, or an ensemble of two or more of: a least absolute shrinkage and selection operator (Lasso)-regularized multivariate Cox-regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, a LASSO model, an elastic net, a Gaussian process classification, or a nearest neighbors classification.

9. The non-transitory computer-readable medium of claim 1, wherein the one or more clinico-pathological factors comprise at least one of a lympho-vascular invasion (LVI) or an American Joint Committee on Cancer (AJCC) stage.

10. An apparatus, comprising:
a memory configured to store a medical imaging scan of a tumor; and
one or more processors configured to:
segment a peri-tumoral region around the tumor;
extract one or more intra-tumoral radiomic features from the tumor and one or more peri-tumoral radiomic features from the peri-tumoral region;
provide the one or more intra-tumoral radiomic features and the one or more peri-tumoral radiomic features to a trained machine learning model;
receive a radiomic risk score (RRS) associated with the tumor from the trained machine learning model, wherein the trained machine learning model generates the RRS based on the one or more intra-tumoral radiomic features and the one or more peri-tumoral radiomic features;
determine a clinical-radiomics score based on the RRS and one or more clinico-pathological factors;
construct a nomogram that visually represents a connection between the RRS and the clinical-radiomics score; and
predict disease free survival for a patient based on the clinical-radiomics score and the RRS depicted in the nomogram.

11. The apparatus of claim 10, wherein the trained machine learning model generates the RRS by applying a regression model to the one or more intra-tumoral radiomic features and the one or more peri-tumoral radiomic features.

12. The apparatus of claim 10, wherein at least one of the one or more intra-tumoral radiomic features or the peri-tumoral radiomic features comprise a first-order statistic of one or more of the following, extracted from the one of the medical imaging scan or the medical imaging scan after transformation with one of a filter or a wavelet decomposition: at least one Laws energy measure, at least one Gabor feature, at least one Haralick feature, at least one Laplace feature, at least one Co-occurrence of Local Anisotropic Gradient Orientations (CoLIAGe) feature, at least one Gray Level Size Zone Matrix, at least one Gray Level Run Length Matrix, at least one Neighboring Gray Tone Difference Matrix, at least one raw intensity value, at least one quantitative pharmacokinetic parameter, at least one semi-quantitative pharmacokinetic parameter, at least one Gray Level Dependence Matrix, at least one shape feature, or at least one feature from at least one pre-trained Convolutional Neural Network (CNN).

13. The apparatus of claim 12, wherein the first-order statistic is one of a mean, a median, a standard deviation, a skewness, a kurtosis, a range, a minimum, a maximum, a percentile, or histogram frequencies.

14. The apparatus of claim 10, wherein the peri-tumoral region comprises a plurality of concentric peri-tumoral rings around the tumor, wherein the one or more peri-tumoral radiomic features comprise at least one peri-tumoral radiomic feature extracted from each peri-tumoral ring of the plurality of concentric peri-tumoral rings.

15. The apparatus of claim 14, wherein each peri-tumoral ring of the plurality of concentric peri-tumoral rings has a width between 2 mm and 4 mm.

16. The apparatus of claim 10, wherein the tumor is an early-stage non-small cell lung cancer (ES-NSCLC) tumor.

17. The apparatus of claim 10, wherein the trained machine learning model is one of, or an ensemble of two or more of: a least absolute shrinkage and selection operator (Lasso)-regularized multivariate Cox-regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, a LASSO model, an elastic net, a Gaussian process classification, or a nearest neighbors classification.

18. A non-transitory computer-readable medium storing computer-executable instructions that, when executed, cause a processor to perform operations, comprising:
    accessing a training set comprising a plurality of medical imaging scans, wherein each medical imaging scan comprises an associated tumor of that medical imaging scan, and wherein, for each medical imaging scan, the associated tumor is associated with a known prognosis and one or more clinico-pathological factors;
    for each medical imaging scan of the training set:
        segmenting a peri-tumoral region around the associated tumor of that medical imaging scan;
        extracting one or more intra-tumoral radiomic features from the associated tumor of that medical imaging scan and one or more peri-tumoral radiomic features from the peri-tumoral region of that medical imaging scan;
    training a machine learning model to generate a radiomic risk score (RRS) based on the known prognosis associated with the associated tumor of that medical imaging scan, the one or more intra-tumoral radiomic features from the associated tumor of that medical imaging scan, and the one or more peri-tumoral radiomic features from the peri-tumoral region of that medical imaging scan; and
    constructing a clinical-radiomics score predictive of tumor prognoses based on the RRS, the one or more clinico-pathological factors for the associated tumor of that medical imaging scan, and the known prognosis for the associated tumor of that medical imaging scan.

19. The non-transitory computer-readable medium of claim 18, further comprising:
    constructing a nomogram to visually represent a connection between the RRS, the clinical-radiomics score, and the known prognosis for the associated tumor.

20. The non-transitory computer-readable medium of claim 18, wherein at least one of the one or more intra-tumoral radiomic features or the peri-tumoral radiomic features comprise a first-order statistic of one or more of the following, extracted from one of that medical imaging scan or that medical imaging scan after transformation with one of a filter or a wavelet decomposition: at least one Laws energy measure, at least one Gabor feature, at least one Haralick feature, at least one Laplace feature, at least one Co-occurrence of Local Anisotropic Gradient Orientations (CoLIAGe) feature, at least one Gray Level Size Zone Matrix, at least one Gray Level Run Length Matrix, at least one Neighboring Gray Tone Difference Matrix, at least one raw intensity value, at least one quantitative pharmacokinetic parameter, at least one semi-quantitative pharmacokinetic parameter, at least one Gray Level Dependence Matrix, at least one shape feature, or at least one feature from at least one pre-trained Convolutional Neural Network (CNN).

* * * * *